(12) United States Patent
Chang et al.

(10) Patent No.: US 8,703,474 B2
(45) Date of Patent: Apr. 22, 2014

(54) FLAVOR COMPOUND-PRODUCING YEAST STRAINS

(75) Inventors: Jui-Jen Chang, Kaohsiung (TW); Cheng-Yu Ho, Bade (TW); Chieh-Chen Huang, Taichung (TW); Ming-Che Shih, Taipei (TW); Wen-Hsiung Li, Yuanshan Township (TW)

(73) Assignee: Academia Sinica, Taipei (TW)

( * ) Notice: Subject to any disclaimer, the term of this patent is extended or adjusted under 35 U.S.C. 154(b) by 82 days.

(21) Appl. No.: 13/210,637

(22) Filed: Aug. 16, 2011

(65) Prior Publication Data
US 2012/0040420 A1    Feb. 16, 2012

Related U.S. Application Data

(60) Provisional application No. 61/374,008, filed on Aug. 16, 2010.

(51) Int. Cl.
*C12N 1/16* (2006.01)
*A61K 38/00* (2006.01)

(52) U.S. Cl.
USPC ...... 435/255.4; 435/243; 435/261; 435/255.1

(58) Field of Classification Search
None
See application file for complete search history.

(56) References Cited

U.S. PATENT DOCUMENTS 4,186,252 A * 1/1980 Silhankova .............. 435/120
5,919,991 A * 7/1999 Subbiah .................. 568/810

2004/0072276 A1 * 4/2004 Koltermann et al. ........... 435/23
2006/0257529 A1 * 11/2006 Sommer et al. ................ 426/62
2012/0027897 A1 * 2/2012 Innocenzi ..................... 426/231

OTHER PUBLICATIONS

Sarenens et al. (2008) Parameters affecting ethyl ester production by *Saccharomyces cerevisiae* during fermentation, Appl .Environ. Microbiol., vol. 74, No. 2, pp. 454-461.*
Sarenens et al. (2006) The *Saccharomyces cerevisiae* EHT1 and EEB1 Genes Encode Novel Enzymes with Medium-chain Fatty Acid Ethyl Ester Synthesis and Hydrolysis Capacity, J. Biol. chem., vol. 281, No. 7, pp. 4446-4456.*
Wu et al. (2009) A survey on composition and microbiota of fresh and fermented yak milk at different Tibetan altitudes, Dairy Sci. Technol., vol. 89, pp. 201-209.*
Wojda et al. (2003) 1.Response to high osmotic conditions and elevated temperature in *Saccharomyces cerevisiae* is controlled by intracellular glycerol and involves coordinate activity of MAP kinase pathways, Microbiol., vol. 149, pp. 1193-1204. Microbiology. May 2003;149(Pt 5):1193-204.*
Simova et al. (2002) Lactic acid bacteria and yeasts in kefir grains and kefir made from them, J. Ind. Microbiol. Biotechnol., vol. 28, issue 1, pp. 1-6.*
Laloux et al. (19991) Cloning and sequencing of the inulinase gene of *Kluyveromyces marxianus* var. *marxianus* ATCC 12424, FEBS Lett., vol. 289, issue 1, pp. 64-68.*
Kang et al. (1999) Molecular cloning and sequence analysis of an endo-inulinase gene from *Arthrobacter* sp., Biotechnol., Lett., vol. 21, pp. 569-574.*
Snow N.H. (2002) Head-space analysis in morden gas chromatography, Trends Analy. Chem., vol. 21, pp. 9-10.*

* cited by examiner

*Primary Examiner* — Manjunath Rao
*Assistant Examiner* — Samuel Liu
(74) *Attorney, Agent, or Firm* — Cesari and McKenna, LLP

(57) ABSTRACT

Disclosed are a novel flavor compound-producing yeast strain and methods of using the strain to produce flavor compounds.

14 Claims, 4 Drawing Sheets

FLAVOR COMPOUND-PRODUCING YEAST STRAINS

CROSS-REFERENCE TO RELATED APPLICATIONS

This application claims priority to U.S. Provisional Application No. 61/374,008, filed Aug. 16, 2010, the content of which is incorporated herein by reference in its entirety.

BACKGROUND

Flavorings account for over a quarter of the worldwide food additive market. Most flavoring compounds are produced via chemical synthesis or by extraction from natural materials. However, for various reasons, these methods are either not efficient or not environmentally friendly. An alternative approach for producing flavoring compounds is microbial biosynthesis or bioconversion. Flavoring compounds produced by a microbe can be marketed as "natural" flavors, which can commend higher prices. Yet, the rate of their synthesis is usually low. There is a need for highly efficient flavor compound-producing microbes.

SUMMARY

This invention is based, at least in part, on the unexpected discovery of a novel thermotolerant *Kluyveromyces marxianus* strain. This strain can be used to produce aromatic higher-alcohol and ester flavor compounds from a cheap substrate, such as raw milk, which contains amino acid and fatty acid precursors.

Accordingly, one aspect of this invention features an isolated yeast strain capable of converting a raw material, e.g., phenylalanine, octanic acid, or decanoic acid, to a flavor compound. One exemplary yeast strain, *Kluyveromyces marxianus* strain KY3, possesses protease activity, and can grow at 25° C.-45° C., ferment raw milk, and assimilate one or more of glucose, mannose, galactose, xylose, arabinose, galactose, fructose, rafinnose, glycerol, cellobiose, lactose, and sucrose. Examples of the flavor compound include, but are not limited to, an ethyl octanoate compound, an ethyl decanoate compound, a 2-phenylethylalcohol compound, or a 2-phenylethanylacetate compound. In one example, the strain can convert raw milk to a flavor compound at 25° C. or above. In another, the strain has the ability to convert raw milk to a flavor compound at 30° C. or above. At a higher temperature, the strain can make a flavor compound at a higher rate. In one embodiment, the strain can convert raw milk to a flavor compound at 37° C.-40° C.

In another aspect, the invention features a method of producing a flavor compound. The method includes culturing the above-described yeast strain in a medium under conditions permitting the synthesis of a flavor compound, and purifying the flavor compound from the cultured yeast or the medium. The medium can contain raw milk or other similar materials. Preferably, the strain is cultured at 25° C. or above, e.g., 30-40° C., or 37-40° C., to achieve a high production yield.

In yet another aspect, provided herein is a method of increasing production of a flavor compound by a microorganism. The method includes culturing the microorganism at an elevated temperature in a medium under conditions permitting production of a flavor compound. Generally, the elevated temperature is a higher temperature within the growth temperature range of the microorganism. For example, the elevated temperature can be 25° C. or above (e.g., 30-40° C.). The production of the flavor compound is increased at the elevated temperature as compared to that at a lower growth temperature. The microorganism can be any organism capable of producing a flavor compound, e.g., a *Kluyveromyces* strain.

The above-described yeast strain can also be used for other purposes, including genetic engineering, production of various metabolites (such as ethanol, 1-butanol, iso-butanol, higher alcohols, easters, and flavor compounds), enzymes, fermentated food and alcoholic drinks (including beers, liquors, liqueurs, and wines), and co-culturing processes with other organisms. In one example, a mutant of the above-described strain is made using genetic engineering and recombinant technology known in the art. The mutant strain can have one or more of the above-described KY3's properties, e.g., the ability of converting phenylalanine, octanic acid, or decanoic acid to a flavor compound.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
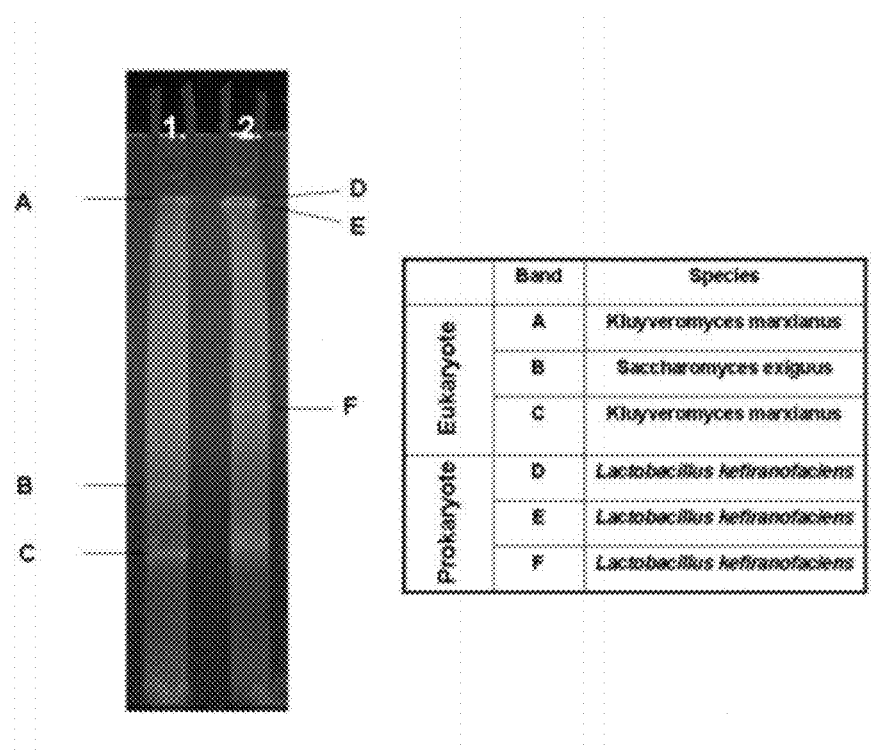
FIG. 1 is a photograph showing the results of bacterioplankton community assay sing partial 26S ribosome rRNA sequences.

As described below, the thermo-tolerant *Kluyveromyces marxianus* strain KY3 was isolated from a special flavor kefir system. This microbe was found to have several advantages, including the ability to grow at a wide temperature range (e.g., 25-45° C.), to utilize a wide variety of carbon sources (e.g., glucose, mannose, galactose, xylose, arabinose, galactose, fructose, rafinnose, glycerol, cellobiose, lactose, and sucrose), to carry out thermophilic ethanol fermentation (optimal at 43° C.) and to produce flavoring pounds such as 2-phenylethylalcohol and 2-phenylethanylacetate. The productivity of 2-phenylethylalcohol (468 µg/ml) of KY3 was found to be higher than those of other species described in the literature. It was found that, at 30° C. and 37° C., the productivity of 2-phenylethanylacetate from raw milk by KY3 is enhanced as compared to at 25° C. In addition, data show that *K. marxianus* KY3 can ferment raw milk at 25° C. to produce octanoic acid-ethyl ester and decanoic acid-ethyl ester compounds, which are not known to be produced by other yeast strains. KY3 was deposited with the Agricultural Research Service Culture Collection (NRRL), 1815 North University Street, Peoria, Ill. 61604, where it was given deposit number NRRL Y-50878.

Accordingly, also provided herein is a method of producing various flavoring compounds, e.g., ethyl octanoate compounds, ethyl decanoate compounds, 2-phenylethylalcohol compounds, and 2-phenylethanylacetate compounds, using *K. marxianus* strain KY3. Conventional techniques, such as those described below, can be used to culture KY3, to produce the flavoring compounds and to purify the compounds thus produced. In addition, a skilled practitioner would be able to scale up the method for industrial applications.

Data described below also show that growing microbes at elevated temperatures can enhance their production of flavor compounds. Thus, provided herein is a method for increasing production of a flavor compound by a microorganism. The method involves culturing the microorganism at an elevated temperature in a medium under conditions permitting production of a flavor compound, whereby production of the flavor compound is enhanced at the elevated temperature. The elevated temperature can be a temperature that is higher than the optimum growth temperature of the microorganism, or a temperature that is at the higher end of the normal growth temperature range of the organism. A skilled practitioner would understand that the elevated temperature selected depends on the microorganism.

The specific example below is to be construed as merely illustrative, and not limitative of the remainder of the disclosure in any way whatsoever. Without further elaboration, it is believed that one skilled in the art can, based on the description herein, utilize the present invention to its fullest extent. Further, any mechanism proposed below does not in any way restrict the scope of the claimed invention. All publications cited herein are hereby incorporated by reference in their entirety.

Isolation and Characterization of *Kluyveromyces marxianus* KY3

(1) Bacterioplankton Community Assay and Microbe Isolation

The special flavor kefir ecosystem that includes yeasts and their syntrophic microbes has been recommended as a dietetic beverage for healthy and sick adults as well as infants. See, e.g., Dimitrellou et al., 2008, Process Biochemistry 43:1323-1329; and Sarkar, 2007, British Food Journal 109 (4): 280-290. We determined the important contributors of the special flavor by profiling the microbe community using denaturing gradient gel electrophoresis (DGGE) and other molecular biology techniques. Our study revealed that *Lactobacillus kefieanofaciens, Kluyveromyces marxianus* and *Saccharomyces exiguus* co-exist in the system. See FIG. 1. The fact that *K. marxianus* was found to be predominant in the population suggests that it contributes to the special flavor of the kefir.

More specifically, according to the kefir's microbial profile by DGGE, and using YPAD (yeast extract 10 g/L, peptone 20 g/L, adenine hemisulfate 24 mg/L, glucose 20 g/L and agar 20 g/L) and LB medium for microorganism isolation, we isolated a novel *K. marxianus* yeast from the kefir system. We made a series dilution of a kefir sample and spread the samples on agar plates, each containing YPAD or LB. Two prokaryotes and three yeasts were isolated from the kefir yogurt. From the growth profile and ethanol production potential of the yeast isolates, only *K. marxianus* strain KY3 showed a broad range of fermentation temperatures and a higher thermo-tolerance than the other isolates (22 to 42° C.).

After isolating chromosomal DNA from strain KY3, DNA fragments of the 26S and 18S ribosome RNA genes were amplified The PCR conditions used were as follows: 95° C. for 5 min, 30 cycles of 95° C. for 1 min, 52-55° C. for 2 min, and 72° C. in 2 min, followed by 72° C. for 7 min. The sizes of the amplified fragments were 300 and 800 base pairs, and the fragments were purified for sequencing analysis. The DNA sequences obtained were used to BLAST the GenBank database. The results showed that the 18S and 26S partial sequences of the KY3 strain are highly homologous to those of *Kluyveromyces marxianus*.

(2) Gene Sequencing and Phylogeny Reconstruction

The *Kluyveromyces* genus has been found to be poly-morphological and so molecular data rather than morphological data should be used to determine the phylogenetic position of a new isolate. Using partial 26S rRNA and 18S rRNA sequences and the neighbor-joining method, we reconstructed the 26S and 18S rRNA trees of *Kluyveromyces* strains.

Figure 2:
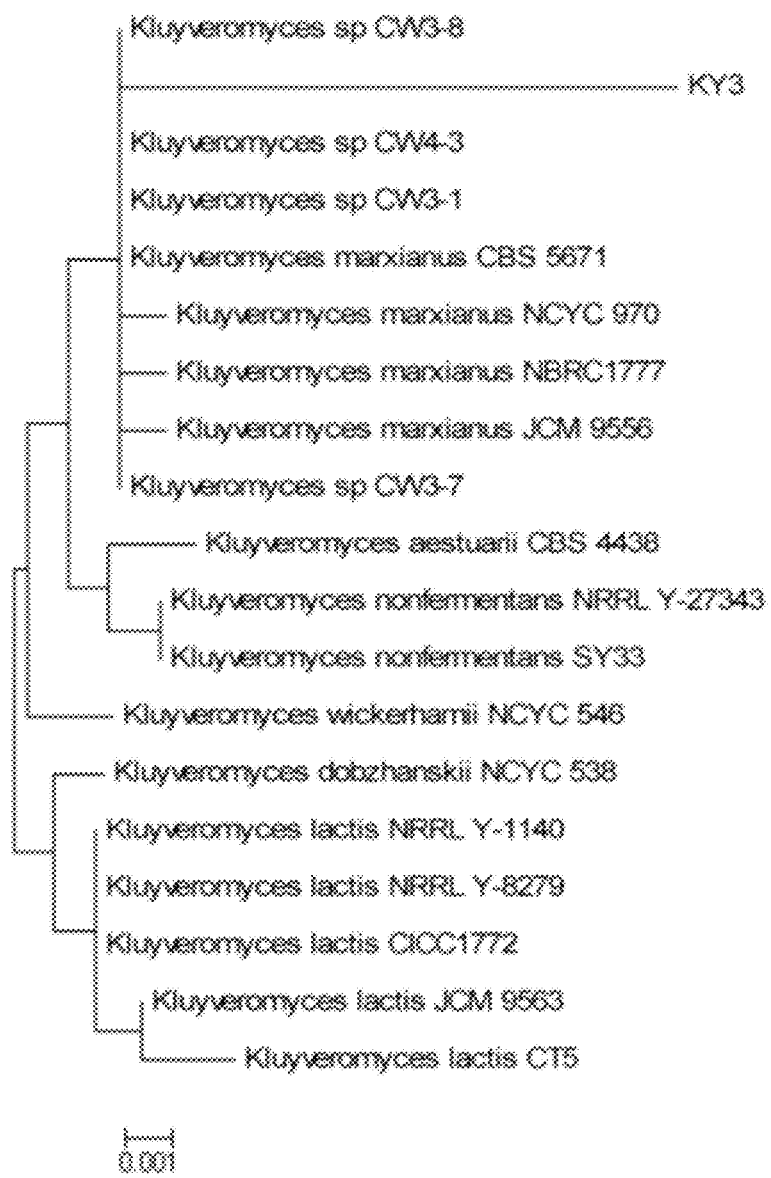
FIG. 2 is a diagram showing the phylogeny of the partial 18S rRNA sequences of KY3 and all available *K. marxianus* strains reconstructed by the neighbor-joining method.

For 26S rRNA partial sequences, most of the strains were found to be identical, as the 500 base pair region is highly conserved. An alignment of the partial 18S rRNA sequences of all known *K. marxianus* strains and KY3 showed that *K. marxianus* KY3 is most similar to Canadian cheese whey isolated *Kluyverromyces* species CW3-8, CW3-4 and CW4-3, whose partial 18SrRNA sequences are identical. Indeed, a BLAST search of the NCBI database showed that the KY3 sequence is most similar to that of CW3-8. A consensus sequence was obtained from the above-described alignment. The CW3-8 sequence is identical to the consensus sequence, whereas the KY3 sequence differs from the CW3-8 sequence and the consensus sequence by 10 nucleotides and 8 indels (i.e., insertions and deletions) within the 1051 aligned positions. As shown in the phylogenic tree of the partial 18S rRNA sequences, *K. marxianus* KY3 has a longer branch length than any of the other *K. marxianus* strains. See FIG. 2. Therefore, we concluded that the Taiwanese kefir isolate *K. marxianus* KY3 is a new strain.

(3) Thermo-Adaptation and Substrate Utilization Tests

To determine temperature adaptation and the potential for ethanol production of KY3, the growth of *K. marxianus* strain KY3, *K. latics* GG799 and *Saccharomyces cerevisiae* BY were examined at 22° C., 30° C., 37° C., 40° C., 42° C., and 45° C. on YPAD plates supplemented with 2% glucose. After 60 hrs, all yeast strains grew at temperatures below 37° C., but only strain KY3 grew well at 42° C. and 45° C.

To determine protease activity, the same three yeast strains were cultured on plates containing 20 g/L skim milk and 20 g/L LB medium. The sizes of clear zones on the plates showed that KY3 is able to digest proteins better than the other two yeasts, indicating a higher protease activity.

Figure 3:
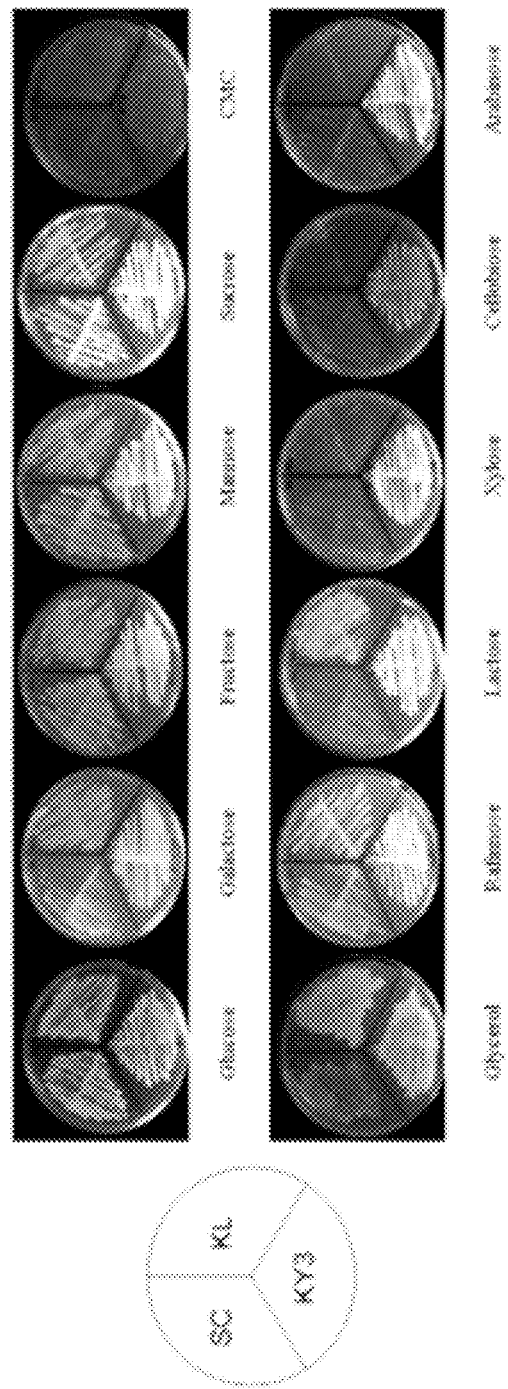
FIG. 3 is a photograph showing the growth of strain KY3 in solid YP medium supplemented with a variety of carbon sources.
Figure 3:
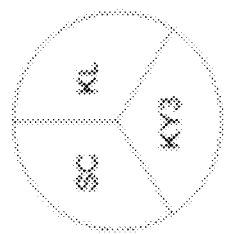

The ability of the three yeast strains to utilize various carbon sources was tested. The strains were grown on solid YP medium supplemented with a variety of carbon sources. The result indicated that all three yeast strains utilize glucose, galactose, fructose, mannose, rafinnose, glycerol and sucrose for growth, but only *K. marxianus* KY3 can also utilize xylose, cellobiose, and arabinose for growth. See FIG. 3.

(4) Production of 2-Phenylethylalcohol and 2-Phenylethanylacetate

Among the major metabolites of yeast fermentation, the higher alcohols such as 2-phenylethylalcohol and 2-phenylethanylacetate are quantitatively the largest groups of volatile components, and their presence is essential to overall flavor quality.

Three *Kluyveromyces* yeast strains, CBS600 (Etschmann et al., 2004, Journal of Molecular Catalysis B: Enzymatic 29:187-193), CBS6432 (Fabre et al., 1997, Biotechnology Techniques, 11(7): 523-525), and strain KY3, were cultivated on a glucose medium supplemented with phenylalanine (2.4 g/l), which is a precursor used as a contributory factor for increasing the production of 2-phenylethylalcohol and 2-phenylethanylacetate. All three strains were able to grow on such medium and produce 2-phenylethylalcohol or 2-phenylethanylacetate from phenylalanine after 192 h incubation at 30° C. under an aerobic or a slightly anaerobic condition.

Under aerobic condition, KY3 produced a slightly higher amount of 2-phenylethanol (0.4686 g/ml) as compared to the other two strains. See Table 1. Under slightly anaerobic condition, strain KY3 produced 0.435 g/ml of 2-phenylethanylacetate, which is a significantly higher level as compared to the other two *K. marxianus* strains. Also see Table 1.

TABLE 1

Yields of 2-phenylethylalcohol and 2-phenylethylacetate by yeasts.

| | Identified compound (uGu)/ml medium | |
|---|---|---|
| Strains | 2-phenylethylalcohol Aerobic/anaerobic | 2-phenylethylacetate Aerobic/anaerobic |
| *K. marxianus* CBS 600 | 418.5/1027.2 | 1.1/99.28 |
| *K. marxianus* KY3 | 468.6/964.7 | 1.0/435.32 |
| *K. marxianus* CBS 6432 | 294.0/880.4 | 0.72/71.94 |

(5) Production of Ethyl Ester Compounds by Ky3 Using Raw Milk as Substrate

Since *K. marxianus* can use lactose and galactose as carbon sources and has protease activity, raw milk, which is a cheap source containing rich amino acids and fatty acids, was chosen as a substrate for ester production. When the fermentation was completed in ten days, *K. marxianus* strain KY3 was found to be able to ferment raw milk at 25° C. and produce some "special flavors" for human smell. These flavors were not produced by other yeasts such as *K. marxianus* strain SSSJ-0, *K. marxianus* strain CBS600, and *K. marxianus* CBS6432, *S. cerevisiae*, and *K. lactis* when they were cultured in raw milk.

To analyze the flavors, samples were taken for volatile compound determination after the fermentation was completed. Solid phase microextraction (SPME) with PDMS fiber was applied to analyze the flavor compounds. The concentrations of the flavor compounds were detected and quantified by GC-MASS with a HP-5MX column. Each fermentation experiment and the subsequent analysis were repeated three times. Our data showed five significant peaks in the sample of *K. marxianus* strain KY3 culture. They were predicted as being phenylethyl alcohol (peak 1), an un-identify compound (peak 2), octanoic acid-ethyl ester (peak 3), acetic acid-2-phenylethyl ester (peak 4), and decanoic acid-ethyl ester (peak 5). See Table 2. Octanoic acid-ethyl ester (peak 3), decanoic acid-ethyl ester (peak 5), and peak 2 are three unique compounds produced by *K. marxianus* strain KY3 using raw milk at 25° C. As peak 2 was a compound not identifiable in the database, it might be a mixture of compounds or a new compound. These three unique compounds likely contribute to the special flavors for human smell.

TABLE 2

The GC-MASS with a HP-5MX column spectrometric data and predicted compounds based on the data.

| Peak | Time | Match/Prob. | |
|---|---|---|---|
| 1 | 4.893 | 790/77.5 | Name: Phenylethyl Alcohol<br>Formula: C8H10O |
| 2 | 5.038 | | Unknown |
| 3 | 5.527 | 837/89.2 | Name: Octanoic acid, ethyl ester<br>Formula: C10H20O2 |
| 4 | 6.113 | 954/63.5 | Name: Acetic acid, 2-phenylethyl ester<br>Formula: C10H12O2 |
| 5 | 7.081 | 602/41.5 | Name: Decanoic acid, ethyl ester<br>Formula: C12H24O2 |

(6) Effect of Temperature on the Production of Flavor Compounds

Figure 4:
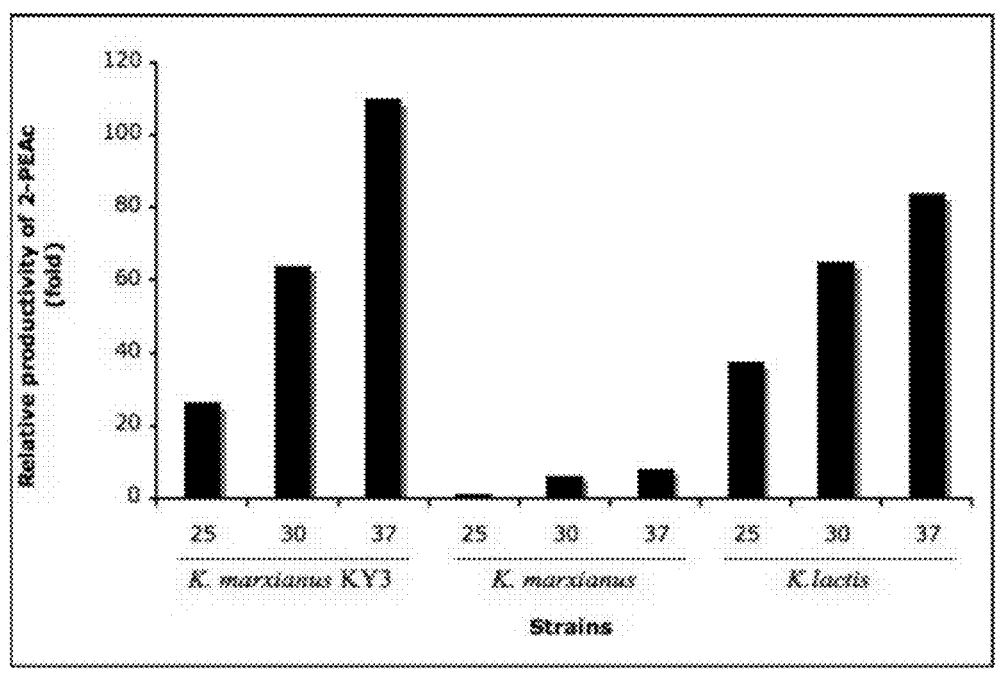
FIG. 4 is a bar graph showing the relative productivities of 2-phenylethylacetate by yeasts under different temperatures.

Strain KY3 was cultured with raw milk for six days at 25° C., 30° C., and 37° C. separately. SPME assay data showed that the production of 2-phenylethanylacetate from raw milk at 30° C. and 37° C. was 2.5-fold and 4-fold higher, respectively, than at 25° C. See FIG. 4. Similarly, for *K. marxianus* strain SSSJ-0 the productivity of 2-phenylethanylacetate at 30° C. and 37° C. was enhanced by 6-fold and 8-fold of the productivity at 25° C. Also see FIG. 4. Interestingly, for *Kluyveromyces lactis*, which cannot grow well at higher temperatures, the production of 2-phenylethanylacetate from raw milk at 30° C. and 37° C. was also enhanced by 1.7-fold and 2.2-fold as compared to at 25° C. See FIG. 4. Thus, raising temperature could enhance production of natural flavorants by microbes, and the effect was amplified in the thermotolerant *K. marxianus* KY3.

To further study the esterification ability of strain KY3, pure amino acid and fatty acid precursors, such as phenylalanine, octanic acid, and decanoic acid, were used as substrates for culturing. It was shown that KY3 can convert these precursors to phenyl ethyl acetate (rose- and honey-like flavor), ethyl octanoate (brandy-like flavor), and ethyl decanoate (coco-like flavor) in two days. The productivities of 2-phenylethanylacetate at 30° C. and 37° C. were also significantly higher than that at 25° C. No significant difference in ester production was found between 30° C. and 37° C.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated yeast strain capable of converting phenylalanine, octanic acid, or decanoic acid to a flavor compound and capable of growing at wide range temperature from 25° C. to 45° C. wherein the strain is *Kluveromyces marxianus* strain KY3, wherein said stain KY3 is isolated by analysis of the 26S and 18S rRNA trees of Kluyveromyces strains in order to identify candidate strain followed by isolation of said candidate strain.

2. The yeast strain of claim 1, wherein the strain exhibits ability to grow at 25° C.-45° C.;
ability to ferment raw milk;
ability to assimilate one or more of glucose, mannose, galactose, xylose, arabinose, galactose, fructose, rafinnose, glycerol, cellobiose, lactose, and sucrose; and a protease activity.

3. The yeast strain of claim 1, wherein the flavor compound is an ethyl octanoate compound, an ethyl decanoate compound, a 2-phenylethylalcohol compound, or a 2-phenylethanylacetate compound.

4. The yeast strain of claim 1, wherein the strain has ability to convert raw milk to a flavor compound at 25° C. or above.

5. The yeast strain of claim 4, wherein the strain has ability to convert raw milk to a flavor compound at 30° C. or above.

6. The yeast strain of claim 5, wherein the strain has ability to convert raw milk to a flavor compound at 37-40° C.

7. A method of producing a flavor compound, the method comprising
culturing the yeast strain of claim 1 in a medium under conditions permitting production of a flavor compound; and purifying the flavor compound from the cultured yeast or the medium.

8. The method of claim 7, wherein the medium contains raw milk.

9. The method of claim 7, wherein the flavor compound is an ethyl octanoate compound, an ethyl decanoate compound, a 2-phenylethylalcohol compound, or a 2-phenylethanylacetate compound.

10. The method of claim 7, wherein the strain has ability to convert raw milk to a flavor compound at 25° C. or above.

11. The method of claim 10, wherein the strain has ability to convert raw milk to a flavor compound at 30° C. or above.

12. The method of claim 10, wherein the strain has ability to convert raw milk to a flavor compound at 37-40° C.

13. The method of claim 7, wherein the culturing step is conducted at 25° C. or above.

14. The method of claim 13, wherein the culturing step is conducted at 37-40° C.

* * * * *